US005766856A

United States Patent [19]
Imani et al.

[11] Patent Number: 5,766,856
[45] Date of Patent: Jun. 16, 1998

[54] DIAGNOSTIC METHOD FOR EVALUATING ADVANCED GLYCOSYLATION ENDPRODUCTS USING MAC-2 RECEPTOR

[75] Inventors: Farhad Imani, Woodbury; Helen Vlassara; Anthony Cerami, both of Shelter Island, all of N.Y.

[73] Assignee: The Picower Institute for Medical Research, New York, N.Y.

[21] Appl. No.: 234,817

[22] Filed: Apr. 28, 1994

Related U.S. Application Data

[60] Continuation-in-part of Ser. No. 10,268, Jan. 28, 1993, Pat. No. 5,316,754, which is a division of Ser. No. 749,444, Aug. 23, 1991, Pat. No. 5,202,424, which is a continuation-in-part of Ser. No. 453,958, Dec. 20, 1989, abandoned, which is a division of Ser. No. 91,534, Sep. 3, 1987, Pat. No. 4,900,747, which is a continuation-in-part of Ser. No. 907,747, Sep. 12, 1986, abandoned, which is a continuation-in-part of Ser. No. 798,032, Nov. 14, 1985, Pat. No. 4,758,583, which is a continuation-in-part of Ser. No. 590,820, Mar. 19, 1984, Pat. No. 4,665,192.

[51] Int. Cl.$^6$ ............................ G01N 33/53; G01N 33/68
[52] U.S. Cl. ........................................ 435/7.1; 436/811
[58] Field of Search ................................ 435/7.1; 436/811

[56] References Cited

U.S. PATENT DOCUMENTS

| 5,202,424 | 4/1993 | Vlassara et al. | 530/395 |
|---|---|---|---|
| 5,316,754 | 5/1994 | Vlassara et al. | 435/7.1 |

FOREIGN PATENT DOCUMENTS

WO 93/04086  3/1993  WIPO.

OTHER PUBLICATIONS

Berkow et al., *The Merck Manual*, 14th edition, pp. 1037–1043, 1842 (1982).
Sparrow et al, "Multiple Soluble β–Glactoside–binding Lectins from Human Lung" *J. Biol. Chem.* 262 (15)7383–7390.
Leffler et al. "Soluble Lactose–Binding Vertebrate Lectins . . . " *Biochem.* 28:9222–9229.
Huflejt et al, "L–29, a Soluble Lactose–binding Lectin . . . " *J. Biol. Chem.* 268 (35):26712–26718.
Knisley et al. "Compartmentalized reactivity of M 3/38 (anti–Mac–2) . . . " *J. Reprod. Fert.* 97: 521–527.
Wollenberg et al, "Human Keratmocytes Release . . . (IgE–Binding Protein) . . . " *J. Exp. Med.* 178: 777–785.
Barondes et al. 1994. Cell 76: 597–98.
Agrwal et al. 1993. J. Biol. Chem. 268: 14932–39.
Koths et al. 1993. J. Biol. Chem. 268: 14245–49.
Lotz et al. 1993. Proc. Natl. Acad. Sci. USA 90:3466–70.
Neeper et al. 1992. J. Biol. Chem. 267: 14998–15004.
Schmidt et al. 1992. J. Biol. Chem. 267:14987–97.
Skolnik et al. 1991. J. Exp. Med. 174: 931–39.
Wang et al. 1991. Glycobiology 1: 243–52.
Yang et al. 1991. J. Exp. Med. 174: 515–24.
Cherayil et al. 1990. Proc. Natl. Acad. Sci. USA 87: 7324–28.
Kirstein et al. 1990. J. Cell Biochem. 14E (Supp.): 76 (#0 224).
Radoff et al. 1990. Diabetes 39:1510–18.
Woo et al. 1990. J. Biol. Chem. 265:7097–99.
Cherayil et al. 1989. J. Exp. Med. 170: 1959–72.
Esposito et al. 1989. J. Exp. Med. 170:1387–1407.
Raz et al. 1989. Cancer Res. 49: 3489–93.
Brownlee et al. 1988. N. Engl. J. Med. 318: 1315–21.
Jia and Wang. 1988. J. Biol. Chem. 263: 6009–11.
Radoff et al. 1988. Arch. Bioch. Biophys. 263:418–23.
Moutsatsos et al. 1986. J. Cell Biol. 102: 477–83.
Vlassara et al. 1986. Diabetes 35.supp (1):13a (#51).
Vlassara et al. 1986. J. Exp. Med. 164:1301–9.
Liu et al. 1985. Proc. Natl. Acad. Sci. USA 82: 4100–04.
Vlassara et al. 1985. Diabetes 34(6):553–57.
Vlassara et al. 1985. Proc. Natl. Acad. Sci. USA 82: 5588–92.
Ho and Springer. 1982. J. Immunol. 128: 1221–28.

*Primary Examiner*—Stephen Walsh
*Assistant Examiner*—Daryl A. Basham
*Attorney, Agent, or Firm*—Klauber & Jackson

[57] ABSTRACT

Soluble and membrane associated forms of Mac-2 (also termed Carbohydrate Binding Protein [CBP]-35 and L-34) recognizes and binds to Advanced Glycosylation Endproducts (AGEs) with higher affinity than it binds carbohydrates, such as its "natural" ligand, galactose. The level of soluble Mac-2 in plasma or serum provides a prognostic indicator of the susceptibility of an individual to AGE complications. Thus, the present invention includes various therapeutic and diagnostic utilities predicated on the identification and activities of Mac-2 for binding AGEs. Pharmaceutical compositions of the invention comprise an effective amount of Mac-2 admixed with a pharmaceutically acceptable carrier. Diagnostic utilities include assays such as immunoassays for the presence and amount of Mac-2 in a biological sample, e.g., serum or plasma. Such assays can be performed with labeled receptors, antibodies, ligands and other binding partners of Mac-2. The invention further provides screening assays to evaluate new drugs by their ability to promote or inhibit Mac-2 production or activity, as desired. The above assays can be used to detect the presence or activity of invasive stimuli, pathology or injury, the presence or absence of which may affect the structure or function of specific organs. In a specific embodiment, the level of soluble Mac-2 varies between different populations of diabetics, and between diabetics and normals.

10 Claims, 6 Drawing Sheets

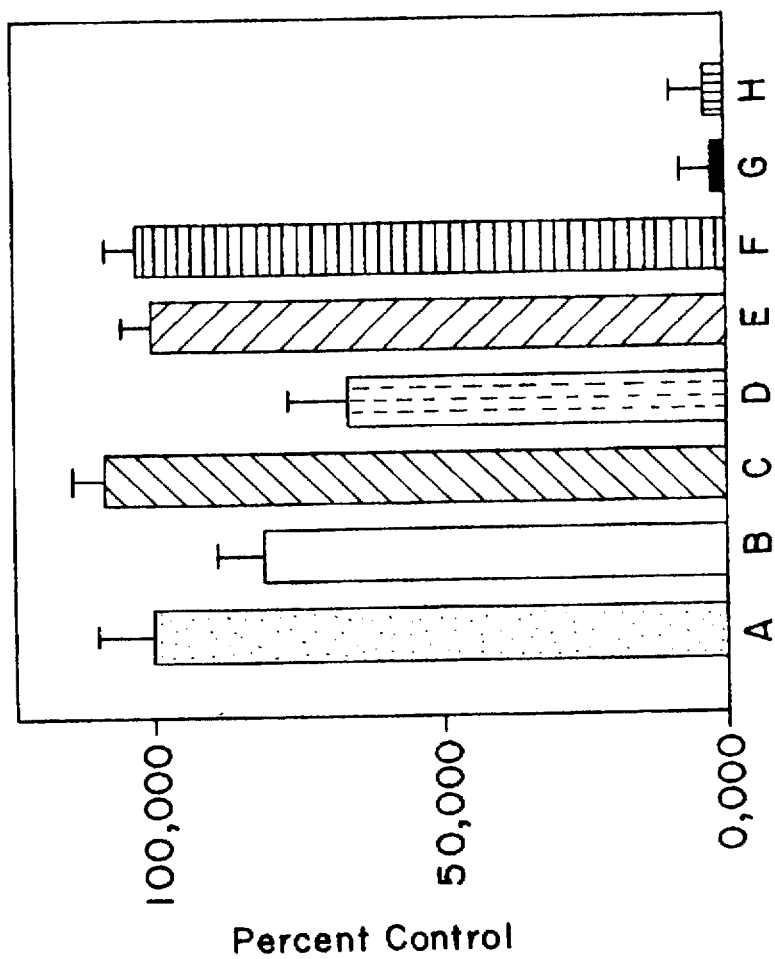

A  B  C

DIAGNOSTIC METHOD FOR EVALUATING ADVANCED GLYCOSYLATION ENDPRODUCTS USING MAC-2 RECEPTOR

The present Application is a continuation-in-part of application Ser. No. 08/010,268, filed Jan. 28, 1993, now U.S. Pat. No. 5,316,754, which is a divisional of application Ser. No. 07/749,444, filed Aug. 23, 1991, now U.S. Pat. No. 5,202,424, which was a continuation-in-part of application Ser. No. 453,958, filed Dec. 20, 1989, now abandoned, which was in turn, a division of application Ser. No. 091,534, filed Sep. 3, 1987, now U.S. Pat. No. 4,900,747, issued Feb. 13, 1990, which was in turn, a continuation-in-part of application Serial No. 907,747, filed Sep. 12, 1986, now abandoned; all of the above preceding applications by Helen Vlassara, Michael Brownlee and Anthony Cerami, said Ser. No. 907,747, in turn, a continuation-in-part of application Ser. No. 798,032, filed Nov. 14, 1985, by Anthony Cerami, Peter Ulrich and Michael Brownlee, now U.S. Pat. No. 4,758,583, which is, in turn, a continuation-in-part of application Ser. No. 590,820, now U.S. Pat. No. 4,665,192, filed Mar. 19, 1984 by Anthony Cerami alone.

The research leading to the present invention was supported by National Institute of Health Grant Nos. AG09453 and AG06943. The Government may have certain rights in the invention.

BACKGROUND OF THE INVENTION

Advanced Glycosylation Endproducts and Receptors Thereto

Glucose and other reducing sugars react non-enzymatically with the amino groups of proteins in a concentration-dependent manner. Over time, these initial Amadori adducts undergo further rearrangements, dehydrations and cross-linking with other proteins to accumulate as a family of complex structures which are referred to as Advanced Glycosylation Endproducts (AGEs). Although this chemistry has been studied by food chemists for many years, it was only in the past decade that the presence of AGEs in living tissue has been established. The excessive deposition of these products on structural proteins as a function of age and elevated glucose concentration, taken together with evidence of effective prevention of tissue pathology by an AGE inhibitor, aminoguanidine, has lent support to the hypothesis that the formation of AGEs plays a role in the long term complications of aging and diabetes.

In vivo formation of AGE-proteins proceeds slowly under normal ambient glucose concentrations, while the rate of AGE-accumulation is markedly accelerated in the presence of hyperglycemia, as occurs in diabetes mellitus (Monnier and Cerami, 1983, Biochim. Biophys. Acta 760:97–103; Monnier et al., 1984, Proc. Natl. Acad. Sci. USA 81:583–87). Numerous studies suggest that AGEs play an important role in the structural and functional alterations which occur in senescence and long-term diabetes (Brownlee et al., 1988, N. Engl. J. Med. 318:1315–21).

Since the amount of AGEs found in human tissues is less than could be predicted from protein/glucose incubation studies in vitro, it appeared that there might be normal mechanisms to remove those long-lived proteins which had accumulated AGEs in vivo. Particularly, and as set forth initially in parent application Ser. No. 907,747, now abandoned and the above-referenced applications that have followed, monocytes/macrophages and endothelial cells were found to display high affinity surface binding activity specific for AGE moieties independent of the protein which was AGE-modified. This AGE-receptor was shown to differ from other known scavenger receptors on these cells.

In addition, an endogenous means for the in vivo elimination or removal of advanced glycosylation endproducts was set forth, and corresponding diagnostic applications involving the receptors and including a specific receptor assay were also proposed.

Following this determination, the applicants herein have sought to further nvestigate the identity and role of advanced glycosylation endproduct receptors and possible binding partners, and any consequent diagnostic and therapeutic implications of these investigations, and it is toward this end that the present invention is directed.

The AGE-specific receptor system now includes a variety of tissues and cell types in addition to monocyte/macrophages for which receptor-mediated AGE-protein internalization and digestion was first described. Endothelial and mesangial cells, as well as fibroblasts, have since been shown to specifically bind AGE-modified protein. In macrophages, AGE-protein uptake is accompanied by the release of a variety of potent cytokines and growth factors, which may coordinate processes of normal tissue remodeling. The other cell types do not bind the model compound AGE, FFI, nor are they known to release cytoidnes and growth factors in response to AGE-ligand binding, but each cell type does display distinct functional responses. For example, endothelial cells exhibit enhanced surface procoagulant activity and permeability; and mesangial cells display enhanced matrix protein synthesis; while human fibroblasts increase proliferation upon exposure to AGEs. Thus, it is now well established that the removal of AGE-modified proteins is facilitated through specific cell surface receptors identified first on cells of the monocyte/macrophage lineage (Radoff et al., 1900, Diabetes 39:1510–18) and subsequently on endothelial cells, mesangial cells and fibroblasts (Esposito et al., 1989, J. Exp. Med. 170:1387; Skolnik et al., 1991, J. Exp. Med; Kirstein et al., 1990, J. Cell Biochem. 14E (Suppl.):0224). In addition to the uptake and degradation of AGE-modified proteins by macrophages, studies on the AGE-receptor/ligand interactions have revealed a range of biologically important responses, including chemotaxis, activation, cytokine production, and growth factor secretion (Skolnik et al., supra; Kirstein et al., supra). The properties have led to the hypothesis that the AGE-R complex plays an important role in normal growth and tissue turnover.

AGE-specific affinity precipitation of cell surface proteins in the murine macrophage cell line RAW 264.7 revealed AGE-associated polypeptides at approximately 90 kD and 30 kD (Radoff et al., supra). Furthermore, two AGE-binding proteins designated as p60 and p90, were isolated from rat liver membranes and were partially sequenced (Yang et al., 1991, J. Exp. Med. 174:515–24). In particular, rat liver and mesangial cell-derived receptors of 90 kD, 60 kD, 50 kD, 40 kD, and 30–35 kD have been identified (International Patent Publication No. WO 93/04086).

U.S. Pat. No. 5,202,424 to Vlassara et al. discloses a substantially purified receptor complex derived from mammalian mesangial cells (MCs). The receptor complex possesses the following characteristics:

A. It recognizes and binds with the ligands AGE-BSA, AGE-RNAse and AGE-collagen I in a saturable fashion, having a binding affinity of about $2.0 \pm 0.4 \times 10^6$ $M^{-1}$ (500 nM);

B. It recognizes and binds to AGE-BSA which has been reduced with $NaBH_4$;

C. It does not recognize and bind with the ligand FFI-BSA, nor with unmodified BSA, RNAse or collagen I in a solid phase ligand blotting assay; and D. It comprises at least three proteins, the first of said proteins having a molecular mass of about 50 kD, the second of said proteins having a molecular mass of about 40 kD and the third of said proteins having a molecular mass of about 30–35 kD, as determined by their migration on SDS-PAGE under reducing conditions.

Antibodies raised against both p60 and p90 recognized surface determinants on rat monocytes and macrophages. These antibodies inhibited AGE binding and neutralized AGE-dependent responses on human monocytes/macrophages, murine mesangial cells and rat T cells, suggesting that the AGE-receptor system involves highly conserved proteins.

The inventors herein are authors or coauthors on many publications relating to AGE receptors, including the following: "FUNCTION OF MACROPHAGE RECEPTOR FOR NONENZYMATICALLY GLYCOSYLATED PROTEINS IS MODULATED BY INSULIN LEVELS", Vlassara, Brownlee and Cerami, DIABETES (1986), Vol. 35 Supp. 1, Page 13a; "RECOGNITION AND UPTAKE OF HUMAN DIABETIC PERIPHERAL NERVE MYELIN BY MACROPHAGES", Vlassara, H., Brownlee, M., and Cerami, A. DIABETES (1985), Vol. 34, No. 6, pp. 553–557; "HIGH-AFFINITY-RECEPTOR-MEDIATED UPTAKE AND DEGRADATION OF GLUCOSE-MODIFIED PROTEINS: A POTENTIAL MECHANISM FOR THE REMOVAL OF SENESCENT MACROMOLECULES", Vlassara H., Brownlee, M., and Cerami, A., PROC. NATL. ACAD. SCI. U.S.A. (Sept. 1985), Vol. 82, pp. 5588–5592; "NOVEL MACROPHAGE RECEPTOR FOR GLUCOSE-MODIFIED PROTEINS IS DISTINCT FROM PREVIOUSLY DESCRIBED SCAVENGER RECEPTORS", Vlassara, H., Brownlee, M., and Cerami, A. JOUR. EXP. MED. (1986), Vol. 164, pp. 1301–1309; "CHARACTERIZATION OF A SOLUBILIZED CELL SURFACE BINDING PROTEIN ON MACROPHAGES SPECIFIC FOR PROTEINS MODIFIED NONENZYMATICALLY BY ADVANCED GLYCOSYLATION END PRODUCTS", Radoff, S., Vlassara, H. and Cerami, A., ARCH. BIOCHEM. BIOPHYS (1988), Vol. 263, No. 2, pp. 418–423; "ISOLATION OF A SURFACE BINDING PROTEIN SPECIFIC FOR ADVANCED GLYCOSYLATION ENDPRODUCTS FROM THE MURINE MACROPHAGE-DERIVED CELL LINE RAW 264.7", Radoff, S., Vlassara, H., and Cerami, A., DIABETES, (1990), Vol. 39, pp. 1510–1518; "TWO NOVEL RAT LIVER MEMBRANE PROTEINS THAT BIND ADVANCED GLYCOSYLATION ENDPRODUCTS: RELATIONSHIP TO MACROPHAGE RECEPTOR FOR GLUCOSE-MODIFIED PROTEINS", Yang, Z., Makita, Z., Horii, Y., Brunelle, S., Cerami, A., Sehajpal, P., Suthanthiran, M. and Vlassara, H., J. EXP. MED., (1991), Vol. 174, pp. 515–24). All of the foregoing publications and all other references cited herein are incorporated by reference.

An additional receptor for advanced glycosylation end products of proteins (termed "RAGE"), a 35 kD polypeptide with a unique $NH_2$-terminal sequence isolated from endothelial cells, has been identified (Schmidt et al., 1992, J. Biol. Chem. 267:14987–97; Neeper et al., 1992, J. Biol. Chem. 267:14998–15004).

Mac-2 Protein

Murine Mac-2 was initially shown to be expressed on the surface of inflammatory macrophages (Ho and Springer, 1982, J. Immunol. 128:1221–28). cDNAs encoding Mac-2 have been obtained. The protein was shown to be secreted and to have the characteristics of a galactose-specific lectin (Cherayil et al., 1989, J. Exp. Med. 170:1959–72); a human Mac-2 lectin specific for galactose has also been cloned (Cherayil et al., 1990, Proc. Natl. Acad. Sci. USA 87:7324–28). The murine protein was independently identified on the basis of carbohydrate binding as carbohydrate-binding protein 35 (CBP 35) in mouse fibroblasts, and on the basis of nuclear localization (Jia and Wang, 1988, J. Biol. Chem. 263:6009–11; Moutsatsos et al., 1987, Proc. Natl. Acad. Sci. USA 84:6452–56). The same protein (named L-34) has also been identified as a tumor cell surface lectin (Raz et al., 1989, Cancer Res. 49:3489–93). Both Mac-2 and a highly similar rat cytosolic protein have the ability to bind murine IgE (Liu et al, 1985, Proc. Natl. Acad. Sci. USA 82:4100–04; Cherayil et al., 1989, supra). Mac-2 has also been found to bind to laminin (Woo et al., 1990, J. Biol. Chem. 265:7097–99, Cherayil et al., 1990, supra). Mac-2, and other S-type lectins, are found in the nucleus, where these proteins are responsible for binding of various neoglycoproteins (Wang et al., 1991, Glycobiology 1:243–252). Under the auspices of an international agreement, Mac-2 is now referred to as galactin-3 (Barondes et al., 1994, Cell 76:597–8).

Decreased expression of Mac-2, and exclusion from the nucleus with preferential localization of the protein in the cytoplasm correlates with neoplastic progression of colon carcinoma (Lotz et al., 1993, Proc. Natl. Acad. Sci. USA 90:3466–70).

The citation of any reference herein is not an admission that such reference is available as prior art to the instant invention.

SUMMARY OF THE INVENTION

In accordance with the present invention, it has been found that the lectin Mac-2 (also termed Carbohydrate Binding Protein [CBP]-35 and L-34) surprisingly recognizes and binds to Advanced Glycosylation Endproducts (AGEs). Both the soluble and cell membrane-associated forms of Mac-2 were found to bind to AGES. More unexpectedly, Mac-2 binds AGEs with higher affinity than it binds carbohydrates, such as its "natural" ligand, galactose.

It has also been found that the level of soluble Mac-2 in plasma or serum provides a prognostic indicator of the susceptibility of an individual to AGE complications.

Accordingly, the present invention includes various therapeutic and diagnostic utilities predicated on the identification and activities of Mac-2 for binding AGES.

Therapeutic uses, including methods and compositions, are based on the property of Mac-2 to bind AGEs and to shepherd the AGEs for metabolism and secretion. Pharmaceutical compositions of the invention comprise an effective amount of Mac-2 admixed with a pharmaceutically acceptable carrier. Such compositions can be prepared for a variety of protocols, including where appropriate, oral and parenteral administration. Exact dosage and dosing schedules are determined by the skilled physician.

Diagnostic utilities include assays such as immunoassays for the presence and amount of Mac-2 in a biological sample, e.g., serum or plasma. Such assays can be performed with labeled receptors, antibodies, ligands and other binding partners of Mac-2. The invention further provides screening assays to evaluate new drugs by their ability to promote or inhibit Mac-2 production or activity, as desired. The above assays can be used to detect the presence or activity of invasive stimuli, pathology or injury, the presence or absence of which may affect the structure or function of specific organs.

The ligands useful in the diagnostic procedures of the present invention are generally AGE derivatives that bind to AGE binding partners. Suitable ligands are selected from the reaction products of reducing sugars, such as glucose and glucose-6-phosphate (G6P), fructose and ribose. These sugars are reactive with peptides, proteins and other biochemicals such as BSA, avidin, biotin, and enzymes such as alkaline phosphatase. The ligands can be labeled, or attached to a solid phase support, for use in assays to detect the presence of, and, if desired, measure the amount of, Mac-2 in a sample suspected of containing Mac-2.

Accordingly, it is a principal object of the present invention to provide a method for evaluating the susceptibility of an individual for AGE complications by measuring the level of Mac-2 in a biological sample from the individual.

It is a further object of the present invention to provide a method as aforesaid which is characterized by the discovery and use of the binding affinity of Mac-2 for advanced glycosylation endproducts.

Yet a further object of the present invention is to provide a method for treating AGE complications by administering Mac-2 to shepherd out the AGEs.

Accordingly, still a further object of the invention is to provide pharmaceutical compositions comprising Mac-2.

These and other objects and advantages of the present invention will become apparent to those skilled in the art from the teachings herein.

BRIEF DESCRIPTION OF THE DRAWINGS

FIG. 4 depicts the ability of various putative ligands to compete with $^{125}$I-labeled AGE-BSA for binding to Mac-2 from whole cell extracts. After immunoprecipitation with anti-Mac-2 MAb, the precipitate was subjected to ligand blot analysis with 300 nM $^{125}$I-AGE-BSA and either no inhibitor (a), or in the presence of a 100 mM (300,000-fold excess) of lactose (b), galactose (c), galactosamine (d), glucosamine (e), Amadori-BSA (f; the concentration of Amadori-BSA was 1.5 mM, a 500-fold excess), cold AGE-BSA (g; the concentration of cold AGE-BSA was 1.5 mM, or a 50-fold excess), or FFI-human albumin (HA) (h; the concentration of FFI-HA was 1.5 mM) competitors. The level of bound radioactivity was measured using phosphoimage analysis.

DETAILED DESCRIPTION OF THE INVENTION

Figure 1:
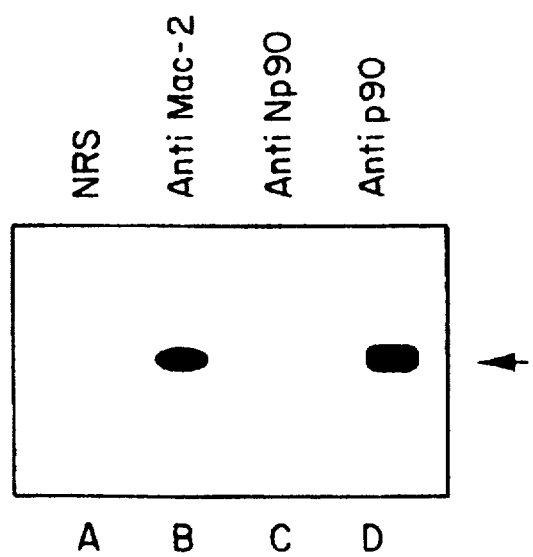
FIG. 1 depicts an immunoblot analysis that shows that anti-P90 recognizes recombinant Mac-2. Purified, recombinant Mac-2 (rMac-2) was subjected to SDS-PAGE and Western blot analysis. Normal rat sera (Lane A, NRS) and polyclonal antisera specific for a synthetic N-terminal peptide of the p90 AGE receptor (Lane C, Anti-Np90) did not react with rMac-2; anti-Mac-2 monoclonal antibody M3/38 (Ho and Springer, 1982. J. Immunol. 128:1221–28) (Lane B, Anti Mac-2), and polyclonal antisera raised against intact p90 (Yang et al., 1991. J. Exp. Med. 174:515–24) (Lane D, Anti p90) reacted with Mac-2.

The present invention is directed to diagnostic and therapeutic methods based on the unexpected discovery that Mac-2 binds to advanced glycosylation endproducts (AGEs) with high affinity, and that this binding activity is substantially non-competitive with binding of carbohydrates to Mac-2. Accordingly, the invention relates to methods for treating diseases and disorders associated with increased levels of AGEs, and compositions for the same. The invention is also directed to methods for determining a prognosis of AGE complications in a patient suffering from an AGE-associated disease or disorder by measuring the level of Mac-2 in serum. While not intending to be limited by any particular theory or hypothesis, it is believed that higher levels of Mac-2 are indicative of an enhanced capacity to clear AGEs; decreased levels of Mac-2 indicate that the AGE clearance mechanisms are not operating efficiently, thus allowing a build-up of AGEs, possibly leading to AGE complications.

As used herein, the term "AGE-" refers to the compound which it modifies as the reaction product of either an advanced glycosylation endproduct or a compound which forms AGEs and the compound so modified, such as the bovine serum albumin (BSA). Thus, AGEs include, but are not limited to, AGE-proteins (such as BSA-AGE), AGE-lipids, AGE-peptides, and AGE-DNA. AGE polypeptides or AGE proteins can be formed in vitro or in vivo by reacting a polypeptide or protein with an AGE, such as AGE-peptide, or with a compound such as a reducing sugar, e.g., glucose, until the polypeptide or protein is modified to form the AGE-polypeptide or protein.

The term "glycosylation" is used herein to refer to the non-enzymatic reaction of reducing sugars with a nucleophile, in particular an amine group, on a polypeptide or protein, such as hemoglobin, a lipid, or DNA, which leads to formation of AGEs. These processes are well known in the art, as described above. Recently, the term "glycation" has become more favored to refer to non-enzymatic glycosylation processes. Thus, the term "glycosylation," as specifically defined herein, and "glycation" are equivalent.

As used throughout the present application, the term "receptor complex" includes both the singular and plural and contemplates the existence of a single receptor structure comprised as all or part thereof, of the individual proteins defined herein, or a plurality of receptor structures respectively constituted in whole or in part by individual of said proteins.

The term "Mac-2" or "Mac-2 protein" is used herein to refer to galactin-3, or a fragment thereof, capable of binding to AGEs. In one embodiment, the protein is a full length protein, e.g., as described in Cherayil et al, 1989, J. Exp. Med. 170:1959–72 [murine Mac-2], and Cherayil et al., 1990, Proc. Natl. Acad. Sci. USA 87:7324–28 [human Mac-2]). In another specific embodiment, a Mac-2 protein can be an 18 kD C-terminal truncated fragment of Mac-2 with AGE-binding activity (e.g., Agrwal et al., 1993, J. Biol. Chem. 268:14932). In a preferred embodiment, a Mac-2 protein of the invention binds to receptors on cells that mediate protein clearance. For example, Mac-2 may bind to an approximately 90 kD scavenger receptor (Koths et al., 1993, J. Biol. Chem. 268:14245–49).

The abbreviation "FFI" refers to the model AGE 2-(2-furoyl)-4(5)-(2-furanyl)-1H-imidazole, which can be reacted with a protein, e.g., BSA, by adding 100 mM carbodiimide to form the adduct FFI-BSA.

A composition comprising "A" (where "A" is a single protein, cell, etc.) is substantially free of "B" (where "B" comprises one or more contaminating proteins, cells, etc.) when at least about 75% by weight of the proteins (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness, and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "pharmaceutically acceptable carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solutions, such as saline solutions and aqueous dextrose and glycerol solutions, are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

The present invention is based, in part, on the discovery that a soluble form of Mac-2 is found in the circulation, and that elevated levels of Mac-2 are found in the circulation of diabetic patients. Also, as mentioned above, the invention further is based on the discovery that Mac-2 is an AGE-binding protein.

A more important discovery is that a subset of diabetic patients have markedly elevated levels of Mac-2, compared to the level in normals or in other diabetics. This discovery suggests that Mac-2 may be a sensitive diagnostic or prognostic indicator based on evaluation of the severity of AGE complications in individuals suffering from a disease or disorder associated with AGE formation by detecting the level of circulating Mac-2.

In one aspect, it appears that high levels of circulating Mac-2 indicate a high level of AGE-receptor activity. AGE receptors bind AGEs and remove them from the body. Thus, elevated levels of AGE-receptor activity may indicate that the endogenous AGE clearance systems in place in the body are operating effectively. If AGEs are cleared, then the likelihood of complications lessens.

If, on the other hand, the level of circulating Mac-2 decreases, it may indicate a general decrease in AGE receptor activity, allowing a build-up of AGEs, and increasing the likelihood of AGE-associated complications.

Accordingly, it is believed that administration of Mac-2 to patients with a disease or disorder associated with AGEs can augment the natural process of eliminating AGEs. For this reason, administration of Mac-2 to patients with a disease or disorder associated with AGE formation may be therapeutically beneficial. Administration of Mac-2 is especially indicated for individuals with decreased levels of circulating Mac-2.

To provide a more complete understanding of the invention, the specification is divided into two sections: one relating to therapeutics; the other relating to diagnostics.

Therapeutic Methods and Compositions

As the Mac-2 AGE receptor appears to play a role in the recognition and removal of advanced glycosylation end-products in vivo, the present invention contemplates therapeutic applications for the soluble form of this protein, or an AGE-binding portion thereof. Thus, Mac-2 may be prepared for administration in various scenarios for therapeutic purposes, in most instances to assist in reducing the concentration of AGEs in vivo.

A Mac-2 protein can be obtained from any source. For example, it may be purified from cell culture fluid of cell lines that endogenously express Mac-2, or from recombinant cell lines that have been engineered to express Mac-2 or an AGE-binding portion thereof (see, e.g., Agrwal et al., 1993, J. Biol Chem. 268:14932). These techniques are described in detail, infra. In a specific embodiment, Mac-2 is recombinant murine Mac-2 obtained as described. Nucleic acids encoding Mac-2 are described in various publications, as noted above (see Cherayil et al., 1989, J. Exp. Med. 170:1959–72 [murine]; Cherayil et al., 1990, Proc. Natl. Acad. Sci. USA 87:7324–28 [human]). Alternatively, Mac-2 can be prepared by peptide synthesis.

Also, the Mac-2 protein may be associated with or expressed by a compatible cellular colony, and the resulting cellular mass may then be treated as a therapeutic agent and administered to a patient in accordance with a predetermined protocol.

The AGE-binding domain of the Mac-2 receptor may be identified, e.g., through recombinant techniques such as site directed mutagenesis and expression of truncated fragments and the like. These manipulations are well known to the skilled practitioner, and can be used to modify Mac-2 nucleic acid coding sequences, i.e., genes, to express mutants.

Thus, in accordance with this aspect of the present invention there may be employed conventional molecular biology and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach, Volumes I and II* (D. N. Glover ed. 1985); *Oligonucleotide Synthesis* M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984).

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryots, and are often functional in both types of organisms.

Numerous therapeutic formulations are possible and the present invention contemplates all such variations within its scope. A variety of administrative techniques may be utilized, among them topical applications as in ointments or on surgical and other topical appliances such as, surgical sponges, bandages, gauze pads, and the like. Also, such compositions may be administered by parenteral techniques such as subcutaneous, intravenous and intraperitoneal injections, catheterizations and the like.

Corresponding therapeutic utilities take advantage of the demonstrated activity of the present Mac-2 protein toward advanced glycosylation endproducts. Thus, to the extent that the in vivo recognition and removal of AGEs serves to treat ailments attributable to their presence in an excess concentration, the administration of the present receptor complex and/or the component proteins comprises an effective therapeutic method. Such conditions as diabetic nephropathy, renal failure and the like may be treated and/or averted by the practice of the therapeutic methods of the present invention.

In a further aspect of the invention, it is contemplated that induction of endogenous Mac-2 production may facilitate removal of AGEs from cell nuclei, which may be important in preventing AGE-mediated modifications of DNA (see, U.S. Pat. No. 5,288,615 to Lee et al., issued Feb. 22, 1994, and references cited therein; and Bucala et al., International Patent Publication WO 94/02599, published Feb. 3, 1994).

Average quantities of the active agent effective for a positive therapeutic outcome may vary between different individuals, and in particular should be based upon the recommendations and prescription of a qualified physician or veterinarian, with an exemplary dosage regimen extending to up to about 25 mg/kg/day.

The Mac-2 protein may be prepared in a therapeutically effective concentration as a pharmaceutical composition with a pharmaceutically acceptable carrier, as defined above. Other compatible pharmaceutical agents may possibly be included, so that for example certain agents may be simultaneously co-administered. In a preferred aspect, an inhibitor of AGE-formation is administered with the Mac-2 receptor, to simultaneously induce removal of AGEs and inhibit formation of new AGES.

Thus, the invention provides for administering Mac-2 and an agent that blocks the post-glycosylation step, i.e., the formation of fluorescent or crosslinking chromophores whose presence is associated with, and leads to, the adverse sequelae of glycosylation. An ideal agent would prevent the formation of a chromophore and its associated cross-links of proteins to proteins and trapping of proteins on to other proteins. The ideal agent would prevent or inhibit the longterm, glycosylation reactions that lead to the formation of the ultimate advanced glycosylation end products that are a direct cause of AGE-associated pathology.

An inhibitor of the formation of AGEs includes compounds that react with a carbonyl moiety of an early glycosylation product. Representative of such advanced glycosylation inhibitors are aminoguanidine, lysine and α-hydrazinohistidine. In a specific embodiment, the inhibitor is aminoguanidine (AG) and derivatives thereof. Pharmaceutical compositions and methods involving AG and derivatives thereof are well known, as described in U.S. Pat. Nos. 4,758,583, issued Jul. 19, 1988; No. 4,908,446, issued Mar. 13, 1990; No. 4,983,604, issued Jan. 8, 1991; No. 5,100,919, issued Mar. 31, 1992; No. 5,106,877, issued Apr. 21, 1992; No. 5,114,943, issued May 19, 1992; No. 5,128,360, issued Jul. 7, 1992; No. 5,130,324, issued Jul. 14, 1992; No. 5,130,337, issued Jul. 14, 1992; No. 5,137,916, issued Aug. 11, 1992; No. 5,140,048, issued Aug. 18, 1992; No. 5,175,192, issued Dec. 29, 1992; No. 5,218,001, issued Jun. 8, 1993; No. 5,221,683, issued Jun. 22, 1993; No. 5,238,963, issued Aug. 24, 1993; No. 5,243,071, issued Sep. 7, 1993; and No. 5,254,593, issued Oct. 19, 1993. Other inhibitors of AGE formation are described in U.S. applications Ser. No. 07/652,575, filed Feb. 8, 1991 now U.S. Pat. No. 5,258,381; Ser. No. 07/889,141, filed May 27, 1992, now U.S. Pat. No. 5,356,985; Ser. No. 07/896,854, filed May 15, 1992, now U.S. Pat. No. 5,272,176; Ser. No. 07/986,661, filed Dec. 8, 1992, now abandoned; Ser. No. 07/986,662, filed Dec. 8, 1992, now U.S. Pat. No. 5,358,960; Ser. No. 08/027,086, filed Mar. 5, 1993, now abandoned; and Ser. No. 08/095,095, filed Jul. 20, 1993 now U.S. Pat. No. 5,534,540. Each of the foregoing patents and patent applications is specifically incorporated herein by reference in its entirety.

Diagnostic Methods

The present invention also relates to a variety of diagnostic applications, including methods for the measurement of the presence and amount of Mac-2 in animals, including humans. The methods comprise assays involving in addition to the analyte, one or more binding partners of Mac-2.

Suitable samples for detection of the level of Mac-2 can be selected from blood, plasma, urine, cerebrospinal fluid, lymphatic fluid, and tissue.

Ligands capable of binding to Mac-2 include, but are not limited to, AGE-BSA, prepared as described infra, and the compounds FFI and AFGP, individually and bound to carrier proteins such as the protein albumin. A carrier may be selected from the group consisting of carbohydrates, proteins, synthetic polypeptides, lipids, bio-compatible natural and synthetic resins, antigens and mixtures thereof.

The present invention seeks to diagnose or determine a prognosis of AGE-related complications, monitoring the course of progression or treatment of an AGE-associated disease or disorder, or monitor a therapy for an AGE-associated disease or disorder. Such conditions as age- or diabetes-related hardening of the arteries, skin wrinkling, arterial blockage, and diabetic, retinal and renal damage in animals all result from the excessive buildup or trapping that occurs as advanced glycosylation endproducts increase in quantity. Therefore, the diagnostic method of the present invention seeks to avert pathologies caused at least in part by the accumulation of advanced glycosylation endproducts in the body by monitoring the amount Mac-2, which can act to clear AGEs from the system. In one embodiment, the diagnostic method involves detection of endogenous Mac-2; in another embodiment, the diagnostic method involves detection of exogenously added Mac-2.

The present invention also relates to a method for detecting the presence of stimulated, spontaneous, or idiopathic pathological states in mammals, by measuring the corresponding presence of Mac-2. In one aspect of the invention, the stimulated, spontaneous, or idiopathic pathological state is induced by phagocytic cell, e.g., macrophage, activation against AGEs. More particularly, the activity of macrophages against AGEs may be followed directly by assay techniques such as those discussed herein, through the use of an appropriately labeled quantity of at least one of the binding partners to Mac-2 as set forth herein.

Thus, both Mac-2 and any binding partners thereto that may be prepared, are capable of use in connection with various diagnostic techniques, including immunoassays, such as a radioimmunoassay, using for example, a receptor or other ligand to an AGE that may either be unlabeled or if labeled, then by either radioactive addition, reduction with sodium borohydride, or radioiodination.

In an immunoassay, a control quantity of a binding partner to Mac-2 may be prepared and optionally labeled, such as with an enzyme, a compound that fluoresces and/or a radioactive element, and may then be introduced into a tissue or fluid sample of a mammal believed to be expressing Mac-2. After the labeled material has had an opportunity to react with sites within the tissue, the resulting mass may be examined by known techniques, which may vary with the nature of the label attached. Preferably if such in vivo detection is desired, the radio-label is technetium-99 ($^{99}$Tc), or a magnetic shift reagent label such as gadolinium or manganese, is used as a label.

The presence of Mac-2 activity in animals can be ascertained in general by immunological procedures, which utilize either a binding partner to the Mac-2, or a ligand thereto, or combinations thereof, in which one component is labeled with a detectable label. In a preferred aspect, the presence of Mac-2 is ascertained in an assay that involves an antibody Ab, labeled with a detectable label, or an antibody $Ab_2$ labeled with a detectable label, or a chemical conjugate with a binding partner to Mac-2 labeled with a detectable label. The procedures may be summarized by the following equations wherein the asterisk indicates that the molecular species is labeled, and "M" in this instance stands for Mac-2 under examination:

A. $M + Ab_1 = M^*Ab_1$

B. $M + Ab^* = MAb_1^*$

C. $M + Ab_1 + Ab_2^* = MAb_1Ab_2^*$

D. Carrier $^*M + Ab_1 = $ Carrier$^*MAb_1$

These general procedures and their application are all familiar to those skilled in the art and are presented herein as illustrative and not restrictive of procedures that may be utilized within the scope of the present invention. The "competitive" procedure, Procedure A, is described in U.S. Pat. Nos. 3,654,090 and 3,850,752. Optional procedure C, the "sandwich" procedure, is described in U.S. Patent Nos.

RE 31.006 and 4,016,043, while optional procedure D is known as the "double antibody", or "DASP" procedure.

A further alternate diagnostic procedure employs multiple labeled compounds in a single solution for simultaneous radioimmunoassay. In this procedure disclosed in U.S. Pat. No. 4,762,028 to Olson, a composition may be prepared with two or more analytes in a coordinated compound having the formula: radioisotope-chelator-analyte.

In each instance, Mac-2 forms complexes with one or more binding partners and one member of the complex may be labeled with a detectable label. The fact that a complex has formed and, if desired, the amount thereof, can be determined by the known applicable detection methods.

With reference to the use of an anti-Mac-2 antibody as a binding partner, it will be seen from the above that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. Where used and for purposes of this description, $Ab_1$ will be referred to as a primary or anti-Mac-2 antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

Suitable radioactive elements may be selected from the group consisting of $^3$H, $^{14}$C, $^{32}$P, $^{35}$S, $^{36}$Cl, $^{51}$Cr, $^{57}$Co, $^{58}$Co, $^{59}$Fe, $^{90}$Y, 125I, $^{131}$I, and $^{186}$Re. In the instance where a radioactive label, such as one of the isotopes listed above, is used, known currently available counting procedures may be utilized to detect or quantitate the amount of label.

In the instance where the label is an enzyme, detection may be accomplished by any of the presently utilized colorimetric, spectrophotometric, fluorospectrophotometric, thermometric, amperometric or gasometric techniques known in the art. The enzyme may be conjugated to the advanced glycosylation endproducts, their binding partners or carrier molecules by reaction with bridging molecules such as carbodiimides, diisocyanates, glutaraldehyde and the like. Also, and in a particular embodiment of the present invention, the enzymes themselves may be modified into advanced glycosylation endproducts by reaction with sugars as set forth herein.

Many enzymes which can be used in these procedures are known and can be utilized. The preferred are peroxidase, β-glucuronidase, β-D-glucosidase, β-D-galactosidase, urease, glucose oxidase plus peroxidase, hexokinase plus GDPase, RNAse, glucose oxidase plus alkaline phosphatase, NAD oxidoreductase plus luciferase, phosphofructokinase plus phosphoenol pyruvate carboxylase, aspartate aminotransferase plus phosphoenol pyruvate decarboxylase, and alkaline phosphatase. U.S. Pat. Nos. 3,654,090; 3,850, 752; and 4,016,043 are referred to by way of example for their disclosure of alternative labeling material and methods.

A number of fluorescent materials are known and can be utilized as labels. These include, for example, fluorescein, rhodamine and auramine. A particular detecting material is anti-rabbit antibody prepared in goats and conjugated with fluorescein through an isothiocyanate.

In specific embodiments, infra, a monoclonal antibody and a polyclonal antibody to Mac-2 are labeled and used to detect the presence, and quantitate the amount, of Mac-2 in a sample. In another specific embodiment, a ligand—AGE-BSA—to Mac-2 is labeled and used to detect the presence, and quantitate the amount, of Mac-2 in a sample. In these specific embodiments, the detectable label is $^{125}$I.

Various assay formats are also contemplated by the present invention for detecting the presence, and if desired, the amount, of Mac-2. For example, a direct "sandwich"-type ELISA can be performed, in which an AGE is attached to the solid phase support, and labeled anti-Mac-2 antibody is used to detect binding of Mac-2 to the solid phase AGE. Alternatively, a Mac-2 antibody can be attached to the solid phase support, and a labeled second anti-Mac-2 antibody that does not compete with the first for binding to Mac-2, or a labeled AGE, can be used to detect binding of Mac-2 to the solid phase.

Blotting formats, in which all the proteins from a sample are blotted, e.g., by electroblotting, on a solid support, such as nitrocellulose, for detecting the presence, and if desired, the amount of Mac-2 are also contemplated by the instant invention. In a specific embodiment, infra, after blotting the proteins in a sample on nitrocellulose, Mac-2 is detected using a labeled AGE and a labeled antibody to Mac-2.

The present invention further provides for sample preparation, prior to conducting an assay to determine the presence, and if desired, the amount, of Mac-2 in the sample. For example, the concentration of Mac-2 in the sample can be effectively increased by immunoprecipitation, followed by separation and detection of Mac-2. Separation procedures include, but are not limited to, sodium dodecyl sulfate-polyacrylamide gel electrophoresis (SDS-PAGE), gel permeation (sizing) chromatography, and the like. SDS-PAGE treatment is preferred for use in conjunction with blotting assays.

The present invention includes assay systems that may be prepared in the form of test kits for the quantitative analysis of the extent of the presence of advanced glycosylation endproducts. The system or test kit may comprise a labeled component prepared by one of the radioactive and/or enzymatic techniques discussed herein, coupling a label to a binding partner to Mac-2, such as an antibody or ligand, as listed herein; and one or more additional immunochemical reagents, at least one of which is capable either of binding with the labeled component, its binding partner, one of the components to be determined or their binding partner(s).

In a further embodiment of this invention, commercial test kits suitable for use by a medical specialist may be prepared to determine the presence or absence of Mac-2. Such kits can also be used to determine the amount of Mac-2 in a sample. In accordance with the testing techniques discussed above, one class of such kits will contain at least labeled antibody to or ligand for Mac-2, and may include directions, depending upon the method selected, e.g., "competitive", "sandwich", "DASP" and the like. The kits may also contain peripheral reagents such as buffers, stabilizers, etc.

For example, a first assay format contemplates a bound ligand to which is added the analyte, followed by a labeled antibody to Mac-2. The resulting substrate is then washed, after which detection proceeds by the measurement of the amount of labeled antibody specifically retained on the ligand-modified substance.

Accordingly, a test kit may be prepared for the demonstration of the presence and activity of Mac-2, comprising:

(a) a predetermined amount of at least one labeled immunochemically reactive component obtained by the direct or indirect attachment of an anti-Mac-2 antibody or a Mac-2 ligand to a detectable label;

(b) other reagents; and (c) directions for use of said kit.

More specifically, the diagnostic test kit may comprise:

(a) a known amount of a binding partner to Mac-2 as described above, such as an antibody or ligand, generally bound to a solid phase to form an immunosorbent, or in the alternative, bound to a suitable tag, or plural such end products, etc. (or their binding partners) one of each;

(b) means for detecting binding of Mac-2 to the solid phase reagent;

(c) if necessary, other reagents; and (d) directions for use of said test kit.

In a further variation, the test kit may comprise:

(a) a labeled component which has been obtained by coupling the binding partner of Mac-2 to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between Mac-2 and a specific binding partner thereto.

All of the protocols disclosed herein may be applied to the qualitative and quantitative determination of Mac-2 and to the concomitant diagnosis and surveillance of pathologies in which the accretion of advanced glycosylation endproducts is implicated. Such conditions as diabetes and the conditions associated with aging, such as atherosclerosis and skin wrinkling represent non-limiting examples, and accordingly methods for diagnosing and monitoring these conditions are included within the scope of the present invention.

Both polyclonal and monoclonal antibodies to Mac-2 are contemplated, the latter capable of preparation by well known techniques such as the hybridoma technique, utilizing, for example, fused mouse spleen lymphocytes and myeloma cells. Immortal, antibody-producing cell lines can also be created by techniques other than fusion, such as direct transformation of B lymphocytes with oncogenic DNA, or transfection with Epstein-Barr virus. Specific polyclonal antibodies can be raised. Naturally, these antibodies are merely illustrative of antibody preparations that may be made in accordance with the present invention.

Detection of AGEs Using Mac-2

In another embodiment, Mac-2 protein can be used to detect the presence of, or measure the amount of, AGE in a sample. Generally, such assays of the invention can detect the presence of AGEs in a sample by detection of binding of Mac-2 to a component in the sample. Such assays include controls to eliminate detection of binding of Mac-2 to a non-AGE molecule.

In one embodiment, Mac-2 is used to coat a solid phase support. The solid phase is then contacted with a sample and a labeled AGE. The presence of AGEs in the sample is detected by their ability to compete with a labeled AGE for binding to solid phase Mac-2. Since carbohydrate binding does not affect Mac-2 binding to AGE (as shown in an Example, infra), this assay is specific for Mac-2.

In another embodiment, an AGE can be attached to a solid phase support. The solid support is then contacted with a sample and labeled Mac-2. The presence of AGEs in the sample is detected by their ability to compete with the solid phase AGE for binding to labeled Mac-2. This assay is also specific for detection of AGEs.

In a further embodiment, Mac-2 can be used as either a solid phase reagent or the labeled reagent in a direct sandwich ELISA assay for AGEs. The other AGE binding partner should be an anti-AGE antibody, or alternatively another receptor that binds only AGEs.

Any of the assay formats, labels, and kits discussed above can be applied to this aspect of the invention as well.

The present invention will be better understood from a consideration of the following illustrative examples and data.

EXAMPLE 1

Mac-2 Binds AGEs With High Affinity

Advanced Glycosylation Endproducts (AGEs), the reactive derivatives of non-enzymatic glucose-protein, are implicated in the multi-organ complications of diabetes and aging. An AGE-specific cellular receptor complex (AGE-R), which may be multi-protein complex that mediates AGE removal, as well as other biological responses has been identified. The present Example relates to the role of Mac-2 in such AGE-R complexes.

In the process of screening an expression library using antibody to one of the components of the AGE-R complex (p90), a partial cDNA clone was isolated with homology to the macrophage surface marker Mac-2, also known as carbohydrate-binding protein (CBP). Mac-2 is a cellular and/or secreted protein of 32 kD. To understand the relationship of Mac-2 to the AGE-R complex, the AGE-binding properties of the molecule were investigated. Purified recombinant rat Mac-2 (rMac-2) bound $^{125}$I-AGE-BSA with saturable kinetics (Kd $3.5 \times 10^7$ M$^{-1}$ and was recognized by antibody to AGE-binding protein p90. Immunoprecipitation of whole cell extracts prepared from RAW 264.7 cells with anti-Mac-2 Mab M3/38, followed by $^{125}$I-AGE-BSA ligand blot revealed several Mac-2 associated proteins (30 kD, 35 kD and 50 kD) with AGE-binding activity. Mac-2 binding of $^{25}$I-AGE-BSA was weakly inhibited by a large excess of several known Mac-2 ligands, e.g., lactose but was fully blocked by cold AGE-BSA.

Materials and Methods

Chemicals and reagents. Recombinant rat Mac-2 (eBP) and a recombinantly produced 18 kD carboxyl-terminal fragment of rat Mac-2 (Agrwal et al., 1993, J. Biol. Chem. 268:14932) were used. Bovine serum albumin (BSA) (Fraction V, low endotoxin), bovine pancreatic RNAse, Nonidet P40 (NP-40), and Triton X-100 were purchased from Boehringer Mannheim Biochemicals (Indianapolis, Ind.). Glucose was purchased from Sigma Chemical Co. (St. Louis, Mo.). Sodium $^{125}$I (10 mCi/100 µl) was obtained form New England Nuclear (Boston, Mass.). Nitrocellulose membranes were from Schliecher & Schuell (Keene, N. H.). The chemically synthesized AGE, 2-(2-furoyl)-4(5)-2(2-Furanyl)-1H-imidazole-hexanoic acid (FF1-HA) was prepared as described (Pongor et al., 1984, Proc. Natl. Acad. Sci. USA 81:2684–88).

Preparation and radiolabeling of ligands. AGE-modified bovine serum albumin was prepared by incubation of BSA with 0.5 M glucose at 37° C. for 6 weeks in a 100 mM phosphate buffered saline, pH 7.4, as previously described (Vlassara et al., 1985, Proc. And. Acad. Sci. USA 82:5588). Unincorporated glucose was removed by dialysis against PBS. AGE content was assessed by an AGE-specific ELISA (akita et al., 1992, J. Biol. Chem. 267:5133–38). AGE-BSA contained approximately 300 AGE units per mg (U/mg).

The chemically defined model AGE, FFI-HA, was synthesized and linked to BSA with 100 mM carbodiimide as described previously (Chang et al., 1985, J. Biol. Chem. 260:7970–74).

Ligand radioiodination was performed with carrier-free $^{125}$I using IODO-beads (Pierce), as described in the manufacturer's instructions for use.

Membrane preparation. Murine macrophage-like cells RAW 264.7 grown in monolayer culture were collected by scraping and washed in phosphate buffered saline (PBS), centrifuged at 1000×g for 5 min, and disrupted with a tight Dounce homogenizer in a solution of PBS containing 1 mM EDTA and protease inhibitors (2 mM phenylmethylsulfonylfluoride [PMSF], 10 µg/ml aprotinin, 5 ng/ml pepstatin, 1 mM benzamidine). The nuclei were removed by centrifugation at 1000×g for 10 min. The cellular membranes were isolated from the supernatant by centrifugation at 10,000×g for 20 min. at 4° C. The resulting membrane-enriched fraction was solubilized in PBS containing 0.5% NP-40, and protease inhibitors as stated above. This material was used for ligand and Western blot studies.

In addition, whole cell extracts were prepared by lysing cells in PBS containing 0.5% NP-40 and protease inhibitors. After 10 min. incubation on ice, nuclei and cell debris were removed by centrifugation at 10,000×g for 10 min. Protein concentrations were determined by the method of Bradford (1976, Anal. Biochem. 72:248–54).

Ligand and Western blotting. Pure recombinant Mac-2 (Agrwal et al. supra) or cell membrane preparations were mixed with an equal volume of Laemli 2 X SDS-PAGE sample buffer containing 5 % β-mercaptoethanol and electrophoresed on a 12% SDS-PAGE. Proteins were then electroblotted onto a nitrocellulose filter, as previously described (Towbin et al., 1979, Proc. Natl. Acad. Sci. USA 76:4350–54). For ligand blot analysis, following blocking for 1 hour in a solution of PBS 5 containing 1.5% BSA and 0.1% Triton -100, 1 mM MgCl₂ and 1 mM CaCl₂ (blocking solution), the nitrocellulose filters were probed with $^{125}$I-labeled AGE-BSA (300 nM) in blocking solution, in the presence or absence of a 50-fold excess of unlabelled AGE-BSA. The blots were washed 3 times with PBS containing 0.1% Triton X-100 and exposed to Kodak XAR-5 film at –80° C. Quantitation of bound radioactivity was performed on a Molecular Dynamics phosphorimager and the values were expressed as relative phosphorimage units.

For western blot analysis, following blocking with PBS containing 3% non-fat dry milk, electroblotted proteins were probed with various primary antibodies as indicated in the Results Section, infra, and visualized by using alkaline phosphatase-conjugated secondary antibodies and the NBT-BCIP western blot detection method (Sambrook et al., supra).

Antibodies. Rabbit antisera were raised against a synthetic peptide corresponding to the published NH2-terminal amino acid sequence of a rat liver AGE-binding proteins P90 (Yang et al., 1991, J. Exp. Med. 174:515–24). This antisera was designated anti-Np90. Avian anti-rat polyclonal antibodies, raised against purified rat liver AGE-binding proteins p90, were prepared as described (Yang et al., supra). Rat monoclonal antibody (MAb) specific to murine Mac-2 was purified using protein G-sepharose column (Boehringer Mannheim Biochemicals, Indianapolis, Ind.) from culture supernatants of hybridoma M3/38 (ATCC accession number TIB166) as described (Akerstrom et al, 1985, J. Immunol. 135:2589–92). Isotypic control rat IgG2a was purchased from Zymed Immunochemicals (South San Francisco, Calif.).

Radiolabeling, immunoprecipitation and ligand precipitation. RAW 264.7 cells (approximately 5×10⁶) were surface radiolabeled using lactoperoxidase-catalyzed iodination as described (Soloski et al., 1986, Proc. Natl. Acad. Sci. USA 83:2949–53). After surface iodination, detergent-solubilized whole cell extract was prepared as stated above. Cell extracts were pre-cleared by incubation with BSA-sepharose for 1 hr at 4° C. For immunoprecipitation, 2.5 µg of MAb M3/38 or the isotype control (rat IgG2a) was added and the reactions were allowed to continue for 14 hrs at 4° C. with gentle rocking. To isolate the Ab-Ag complexes, goat anti-rat-agarose (Sigma) was added. After incubation for 2 hrs, the Ab-Ag complexes were isolated by centrifugation at 2,000×g, washed 4 times with PBS containing 0.5% NP-40, and pelleted. An equal volume of 1 X Laemli SDS-PAGE buffer containing 2.5% β-mercaptoethanol was added to the pellets.

For ligand affinity precipitation, AGE-BSA was coupled to activated sepharose-4B as previously described (Yang et al., supra). After preclearing the cell extracts with BSA-sepharose, AGE-BSA-sepharose was added and the reaction was allowed to continue for one hour at 4° C. with gentle rocking. The complexes were separated by centrifugation at 2000×g and washed extensively with PBS containing 0.5% NP-40. An equal volume of 1 X Laemli SDS-PAGE buffer containing 2.5% β-mercaptoethanol was added to the washed ligand affinity precipitate.

For SDS-PAGE analysis of the precipitates from either method, the samples were boiled for two minutes, and the proteins were electrophoresed through a 12% SDS-PAGE gel. Ligand- and immunoprecipitated proteins were visualized by autoradiography of dried gels.

Results

Antibody to the AGE-binding protein p90 recognizes Mac-2. To begin exploring the relationship between the AGE-receptor (AGE-R) proteins and Mac-2, Western blot analysis was performed using recombinant purified rat Mac-2 (rMac-2) and avian polyclonal antibodies raised either against the purified 90 kD subunit of the rat liver membrane AGE-R (anti-p90) or against the NH₂-terminal sequence of p90 (anti-Np90). A single immunoreactive species of 32 KD was readily observed using antibodies to the purified intact p90 (anti-p90) or to rMac-2 (M3/38) FIG. 1, lanes B and D), but not by the antibody to the synthetic N-terminal peptide sequence or by the isotypic control rat IgG2a (FIG. 1, lanes C and A). This was consistent with the possibility that p90 contains an epitope shared by Mac-2 or that p90 itself consists of more than one polypeptide, one of which is Mac-2.

Figure 2:
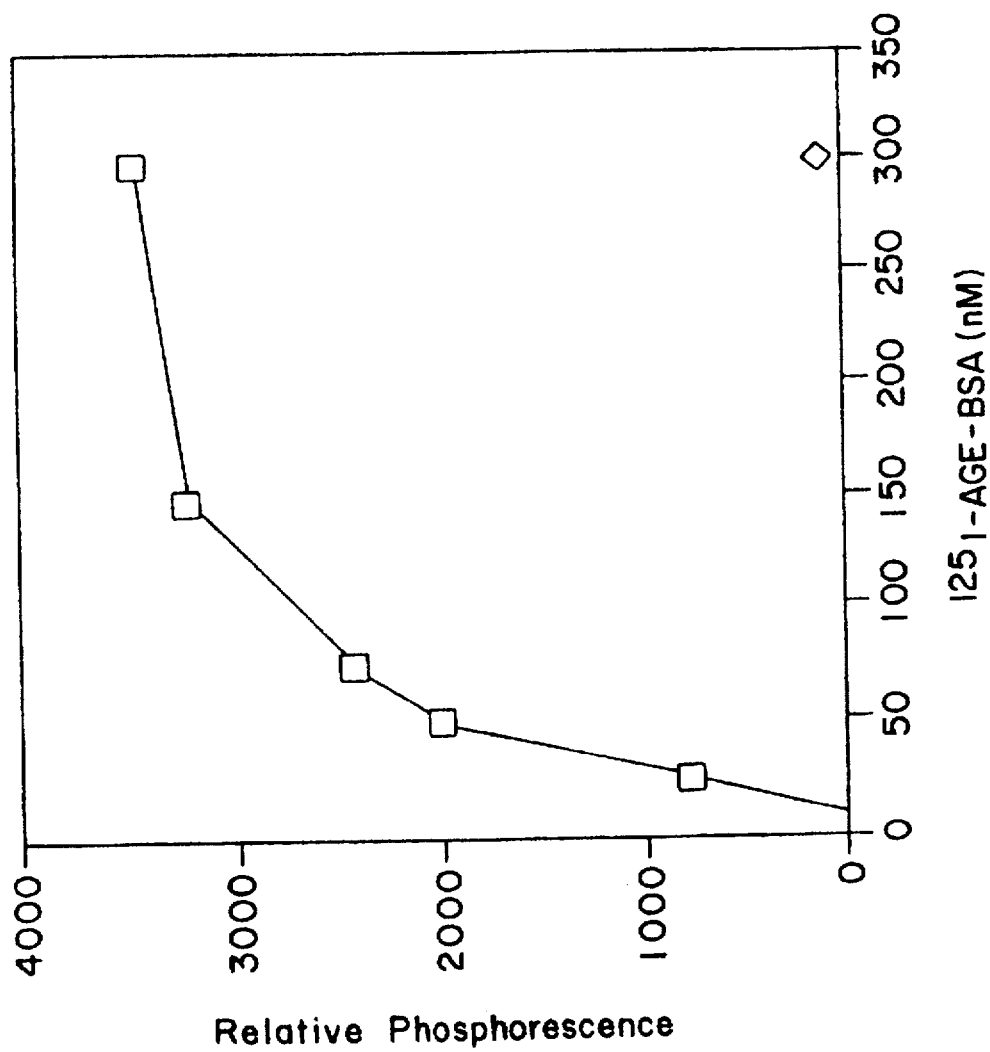
FIG. 2 depicts a graph showing the saturability of AGE binding to Mac-2. Binding of increasing concentrations of $^{125}$I-labeled BSA-AGE to 3 μg of purified rMac-2 immobilized on a nitrocellulose membrane (□) was measured. After washing, the bound radioactivity was measured by phosphoimage analysis. Binding of the highest concentration of labeled AGE-BSA was completely abrogated by competition with a 50-fold excess of cold AGE-BSA (◊).

Recombinant Mac-2 binds AGE-modified proteins. To test whether Mac-2 exhibits AGE-binding activity, purified rMac-2 (3 µg aliquots) was immobilized onto nitrocellulose membrane and probed with increasing amounts of $^{125}$I-AGE-BSA in the presence or absence of a 50-fold excess unlabeled AGE-BSA. As shown in FIG. 2, rMac-2 binding of $^{125}$I-AGE-BSA rose in a concentration-dependent manner. Radioligand binding was saturable and could be completely abrogated by unlabeled AGE-BSA. Scatchard plot analysis of the binding data were consistent with a single class of binding sites and an affinity of $3.5 \times 10^7$ $M^{-1}$. This affinity is similar to that reported previously for the AGE-receptor on macrophages/monocytes (Radoff et al., 1990, Diabetes 39:1510–18).

Figure 3A:
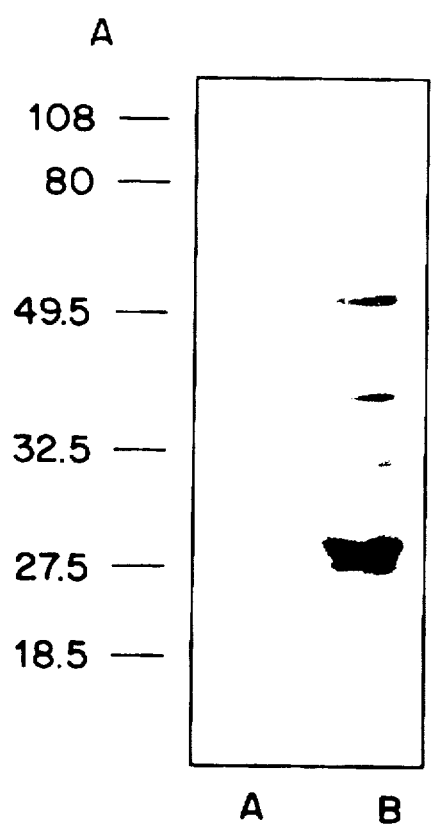
FIG. 3 depicts a blot analysis of anti-Mac-2 immunoprecipitates of several AGE-binding proteins. Panel A. Detergent cell extracts were prepared from RAW 264.7 cells. After preclearing with BSA-SEPHAROSE, immunoprecipitations were performed using isotype control (Lane A), or anti-Mac-2 monoclonal antibody M3/38 (Lane B). After SDS-PAGE and transfer to nitrocellulose, the blots were probed with $^{125}$I-labeled AGE-BSA. Panel B. A purified carboxyl-terminal fragment of Mac-2 was subjected to ligand blot analysis in the absence (Lane A) or presence (Lane B) of a 50-fold excess of cold AGE-BSA.
Figure 3B:
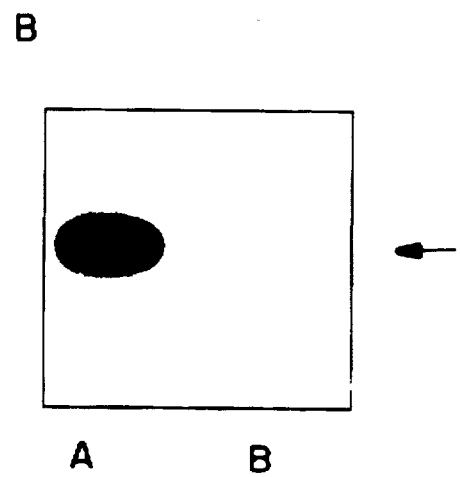

Similar AGE-binding activity was exhibited by Mac-2 immunoprecipitated from cell membrane extracts from the macrophage-like RAW 264.7 cell line using monoclonal antibody M3/38. Anti-Mac-2-reactive material was subjected to SDS-PAGE and, after transfer to nitrocellulose, to Western and ligand blot analysis. Three proteins with apparent molecular weights of 30 KD, 35 KD and 50 KD were precipitated by M3/38. All three proteins displayed $^{125}$I-AGE-binding activity on ligand blotting (FIG. 3A, lane B). AGE-binding activity was also shown by an 18 kD carboxyl-terminal fragment of Mac-2 (FIG. 3B, lane A), and this binding was completely abrogated in the presence of a 50-fold excess unlabeled AGE-BSA (FIG. 3B, lane B). By comparison, isotypic IgG2a antibody failed to precipitate any AGE-binding species (FIG. 3A, lane A). The identity of the 35 KD polypeptide as Mac-2 was confirmed by polyclonal anti-CBP35 antibodies (data not shown).

AGE-Binding to Mac-2/CBP is not inhibitable in the presence of carbohydrates. Several laboratories have identified Mac-2 (CBP35) as a lectin with binding specificity to carbohydrate moieties, e.g., lactose, galactose and galactosamine (Moutsatsos et al., 1986, J. Cell Biol. 102:477–83; Cherayil et al., 1990, Proc. Natl. Acad. Sci. USA 87:7324–28). To test whether Mac-2 AGE-binding domain is the same and/or of comparable affinity to that of carbohydrates, competitive ligand blot inhibition experiments were performed. Equal amounts of Mac-2 immunoprecipitates (approximately equal to that extracted from 2.5×10$^5$ cells per lane) were subjected to SDS-PAGE and electrotransferred onto nitrocellulose. $^{125}$I-AGE-BSA ligand blot analysis (300 nM $^{125}$I-AGE) was performed in the presence or absence of a large excess (100 mM) of lactose, galactose, galactosamine and glucosamine. The addition of lactose, galactose and glucosamine in excess of 300,000-fold (100 mM) failed to significantly alter $^{125}$I-AGE-BSA binding to Mac-2, compared to the complete inhibition achieved by unlabeled AGE-BSA added at 50-fold excess (15 μM) (FIG. 4).

Figure 5:
FIG. 5 presents an autoradiogram of immunoprecipitated or ligand-affinity precipitated, cell surface iodinated RAW 264.7 macrophage cells, after SDS-PAGE. Cell surface proteins were radiolabeled using the lactoperoxidasecatalyzed iodination technique. Detergent extracts were prepared and were subjected to immunoprecipitation with rat IgG$_{2a}$ isotype control (Lane A), anti-Mac-2 monoclonal antibody M3/38 (Lane B), or AGE-BSA conjugated to SEPHAROSE (ligand affinity precipitation) (Lane C). The precipitated proteins were subjected to SDS-PAGE and were visualized by autoradiography.

Cell-surface Mac-2 binds AGE-BSA. Mac-2 has been found as a cytoplasmic, nuclear and, to a lesser extent, as membrane-associated protein. To demonstrate that cell surface Mac-2 is capable of binding AGE-ligands, surface-iodinated macrophage-like RAW 264 cell extracts were used either for immunoprecipitation using M3/38 mAb, or for ligand-affinity precipitation studies, using an AGE-BSA-sepharose affinity system, as described (Yang et al., 1991, supra). In either case, the protein complexes obtained were eluted with SDS-PAGE sample buffer and electrophoresed. As shown in FIG. 5, lane B, autoradiography of the labelled cell-surface complexes immunoprecipitated by M3/38 monoclonal antibody revealed a polypeptide of approximately 32 kD. This was similar to a polypeptide band obtained by ligand-affinity precipitation of the same extracts, exhibiting identical mobility to Mac-2 (FIG. 5, lane C). In addition, using either procedure (immuno- and ligand-affinity precipitation), a polypeptide with the apparent molecular weight of 90 kD was identified (FIG. 5, upper arrow).

Discussion

This Example provides evidence that the macrophage surface marker Mac-2 has a novel property of binding AGES, and this is unexpectedly a member of the AGE-R protein family. Previously, two polypeptides, designated p60 and p90, were identified as AGE-binding proteins, which may comprise portions of an AGE-R complex. A partial cDNA clone corresponding to Mac-2 was isolated while attempting to clone p90 using a protein expression library and antibody recognition of expressed proteins. Western analysis of rMac-2 was performed using antibodies made either to the purified rat liver membrane p90 polypeptide (anti-p90) or to the N-terminal peptide sequence obtained from the respective analysis of this material (anti-N90). The anti-p90 polyclonal antibody recognized Mac-2, suggesting either an immunologic crossreactivity between p90 and Mac-2 or the presence of anti-Mac-2 immunoreactivity in the original antibody preparations.

Possible participation of Mac-2 as an AGE-binding protein was investigated using purified rMac-2. This material proved capable of independently and specifically binding AGE-modified proteins with saturable kinetics (Kd $3.5 \times 10^7$ M$^{-1}$). This binding affinity is comparable to the previously established affinity of the AGE-R present on intact macrophages (Radoff et al., supra), although lower than that of purified rat liver membranes. These differences may reflect either differences between recombinant and biological material or the need for cooperation of more than one AGE-R component for maximal AGE-binding activity.

Several laboratories have characterized Mac-2 as lactose/galactose specific lectin. Based on competitive ligand blot analyses in which lactose, galactose, glucosamine and galactosamine added in large excess failed to effectively displace Mac2-bound AGE, it appears that Mac-2 has a separate binding site for AGEs. In addition, the data suggest that AGE-modified proteins bind Mac-2 with a high affinity. The AGE-binding region appears to lie within an 18 kD carboxyl-terminal fragment of Mac-2, which corresponds to the carbohydrate-binding portion of the molecule. The present data do not definitively distinguish between a single or multiple receptor sites on Mac-2, but it appears that only one functional class of AGE-binding sites are found on Mac-2.

In agreement with previous reports, the presence of Mac-2 on the cell surface was demonstrated by immunoprecipitation of surface-labeled RAW 264.7 cells. Anti-Mac-2 precipitated the expected 32 kD polypeptide, as well as several other molecules with the apparent molecular weights of 25 kD and 50 kD. In addition, affinity precipitation using AGE-BSA-sepharose yielded two polypeptides, one with identical mobility to Mac-2 at 32 KDa, and a 90 KDa polypeptide.

This result indicated that Mac-2 is indeed present on the cell surface. Furthermore, the data are consistent with a model in which Mac-2 binds AGEs possibly in concert with Mac-2-associated polypeptides such as p35, p50, p60, and p90. This receptor complex may function in the removal of AGE-modified proteins from tissue.

Moreover, soluble Mac-2 may interact with circulating AGE-proteins and facilitate their removal by specific cell surface receptors.

Recently, a 90 KDa polypeptide has been identified and designated as Mac-2 binding protein (Koths et al., 1993, J. Biol. Chem. 268:14245–49). This receptor is a candidate for uptake and removal of Mac-2 in the circulation.

Ho and Springer characterized Mac-2 polypeptide as a surface marker for differentiated macrophages (1982, J. Immunol. 128:1221–28). Extensive work by several groups has shown that this molecule is ubiquitously expressed on a variety of cell lines and was present in nuclear, cytoplasmic, membrane bound as well as secreted forms. The presence of Mac-2 in various cellular locations particularly in cell membrane and secreted forms, is intriguing since its cDNA does not code for any known signal sequences. It is possible that Mac-2 is secreted in a similar fashion to IL-1 and MIF, which also lack signal sequences. The presence of Mac-2 on the cell surface is of further interest since there are not transmembrane spanning domains present in this polypeptide. Thus, it is conceivable that this molecule is present on the cell surface in association with other subunits that may comprise an AGE-R complex.

The immunoprecipitation studies reported here, using anti-Mac-2 followed by ligand blot analysis, showed that several other species of AGE-binding proteins with approximate molecular weights of 20 KDa, 35 KDa and 50 KDa, were associated with Mac-2 and were capable of binding $^{125}$I-AGE-BSA.

EXAMPLE 2

Association of Mac-2 With Diabetes

Figure 6:
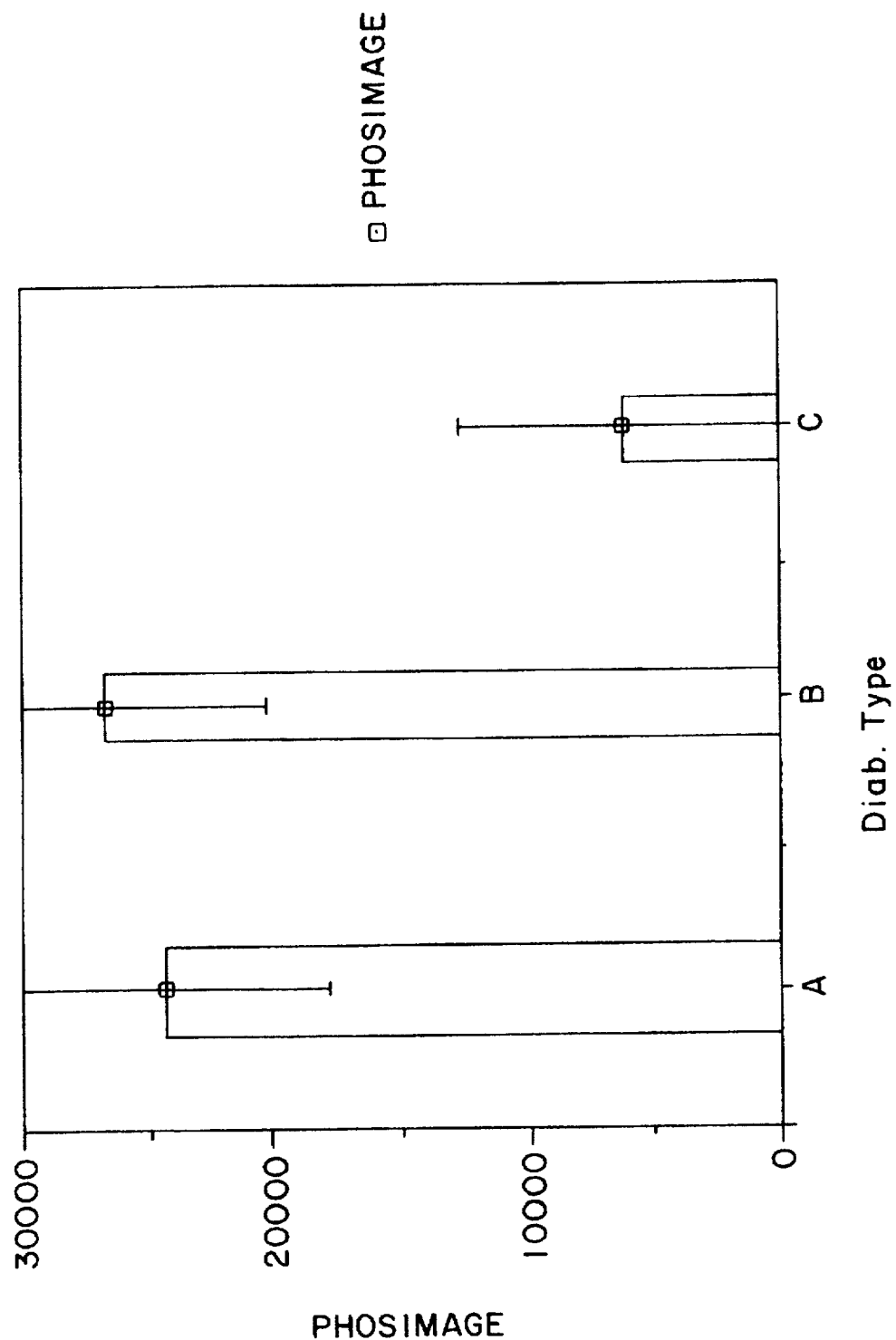
FIG. 6 is a bar graph showing the level of soluble AGE-binding protein to a 32 kD band, presumably Mac-2, in serum samples from Type-I diabetics (A; n=12), Type-II diabetics (B; n=12), and normal individuals (C; n=12). The level of AGE-binding protein in the serum samples was measured by quantitating binding with $^{125}$I-AGE-BSA after SDS-PAGE and transfer to nitrocellulose.

Screening of human diabetic sera (n=22) using the SDS-PAGE-ligand blot analysis described above revealed a 32 kD polypeptide band, migrating identically to Mac-2, which exhibited an average of 5-fold greater AGE-binding activity on ligand blots compared to normal controls (n=13) (p<0.005). These data are shown in FIG. 6. These data clearly demonstrate that binding of a putative Mac-2 protein with $^{125}$I-AGE-BSA in samples from both Type-I and Type-II diabetics is much greater than in samples from normal controls.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

Various references are cited herein, the disclosures of which are incorporated by reference herein in their entirety.

What is claimed is:

1. A method for evaluating the level of activity of receptors for advanced glycosylation endproducts (AGEs) for diagnostic or prognostic purposes comprising detecting the level of soluble Mac-2 in a biological sample from a mammal, and comparing the level of Mac-2 in the sample with the level of Mac-2 in diabetics or in the mammal at an earlier time, wherein an increase in the level of soluble Mac-2 compared with the level found in diabetics or in the mammal at an earlier time correlates with an increase in the level of AGE-receptor activity, wherein an increase in the level of AGE-receptor activity is indicative of reduced likelihood of AGE-associated complications of a disease or disorder associated with AGEs.

2. A method for evaluating the severity of complications of a disease or disorder associated with advanced glycosylation endproducts for diagnostic or prognostic purposes comprising detecting the level of soluble Mac-2 in a biological sample from a mammal, and comparing the level of Mac-2 in the sample with the level of Mac-2 in diabetics or in the mammal at an earlier time, wherein a decrease in the level of Mac-2 compared with a level found in diabetics or in the mammal at an earlier time correlates with a greater likelihood of an increase in the severity of complications of a disease or disorder associated with advanced glycosylation endproducts.

3. A method for evaluating the severity of complications of a disease or disorder associated with advanced glycosylation endproducts for diagnostic or prognostic purposes comprising evaluating the level of activity of receptors for advanced glycosylation endproducts (AGEs), which comprises detecting the level of soluble Mac-2 in a biological sample from a mammal, and comparing the level of Mac-2 in the sample with the level of Mac-2 in diabetics or in the mammal at an earlier time, wherein an increase in the level of soluble Mac-2 compared with a level found in diabetics or in the mammal at an earlier time is indicative of an increase in the level of AGE-receptor activity, and wherein the level of AGE-receptor activity inversely correlates with the severity of complications of the disease or disorder associated with advanced glycosylation endproducts.

4. The method according to claim 1, 2, or 3, wherein the mammal is a human.

5. The method according to claim 1, 2, or 3, wherein the disease or disorder is diabetes.

6. The method according to claim 1, 2, or 3, wherein the disease or disorder is related to ageing.

7. The method according to claim, 1, 2, or 3, wherein the biological sample is selected from the group consisting of blood, serum, plasma, cerebrospinal fluid, and urine.

8. A method for screening for diabetes in a mammal suspected of suffering from diabetes comprising detecting a level of soluble Mac-2 in a biological sample from a mammal suspected of suffering from diabetes, and comparing the level of Mac-2 to a level in normal mammals of the same species, wherein an elevated level in the sample compared to the level in normal mammals of the same species is indicative of diabetes.

9. The method according to claim 8 wherein a level of soluble Mac-2 in the sample is about 5-times higher than the level in a normal mammal is indicative of diabetes.

10. The method according to claim 8 wherein the mammal is a human.

* * * * *